United States Patent [19]

Yano et al.

[11] Patent Number: 4,737,494

[45] Date of Patent: Apr. 12, 1988

[54] 1,3-DITHIOLE DERIVATIVES AND PHARMACEUTICAL COMPOSITIONS

[75] Inventors: Mitsuo Yano, Yokohama; Yoshimi Tsuchiya, Funabashi; Yukio Hirayama, Yokohama; Kyoko Nakamichi; Junji Yoshizawa, both of Tokyo, all of Japan

[73] Assignee: Banyu Pharmaceutical Co., Ltd., Tokyo, Japan

[21] Appl. No.: 813,583

[22] Filed: Dec. 26, 1985

[30] Foreign Application Priority Data

Dec. 26, 1984 [JP] Japan .................. 59-273438

[51] Int. Cl.$^4$ .................. A61K 31/40; A61K 31/535; C07D 409/04; C07D 413/04
[52] U.S. Cl. .................. 514/212; 514/222; 514/230; 514/252; 514/326; 514/342; 514/365; 514/374; 514/422; 540/596; 544/58.4; 544/145; 544/379; 546/207; 546/284; 548/200; 548/201; 548/215; 548/527
[58] Field of Search .............. 540/596; 544/58.4, 145, 544/379; 546/207, 284; 548/200, 201, 215, 527; 514/212, 222, 230, 252, 326, 342, 365, 374, 422

[56] References Cited

PUBLICATIONS

Buza et al., *Chemical Abstracts*, vol. 95, (1981), No. 80779k.

Mas, et al., *Chemical Abstracts*, vol. 88, (1978), No. 22715f.

Yano et al., *Chemical Abstracts*, vol. 106, (1987), No. 176430m.

Yano et al., *Chemical Abstracts*, vol. 105, (1986), No. 208854a.

Yano et al., *Chemical Abstracts*, vol. 105, (1986), No. 172436z.

*Primary Examiner*—Robert W. Ramsuer
*Attorney, Agent, or Firm*—Oblon, Fisher, Spivak, McClelland & Maier

[57] ABSTRACT

A 1,3-dithiole derivative having the formula:

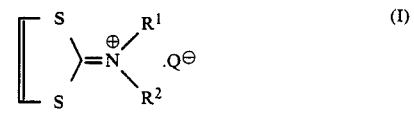

wherein each of $R^1$ and $R^2$ is a substituted or unsubstituted alkyl, cycloalkyl, lower alkenyl, lower alkynyl, aryl or aralkyl group or $R^1$ and $R^2$ together form a substituted or unsubstituted alkylene or alkenylene group having from 3 to 6 carbon atoms, which may contain a cycloalkylene group, an o-phenylene group or a hetero atom selected from the group consisting of an oxygen atom, a sulfur atom and a nitrogen atom which may have a substituent, and Q is an acid residue useful for the treatment of liver diseases.

4 Claims, No Drawings

1,3-DITHIOLE DERIVATIVES AND PHARMACEUTICAL COMPOSITIONS

The present invention relates to novel 1,3-dithiole derivatives, a process for their production and a pharmaceutical composition for treating the liver diseases.

It is known that there are a large number of patients who suffer from liver damages caused by various factors such as alcohol, malnutrition, viruses, chemicals, toxicants, etc. The liver diseases may generally be classified by their types into acute hepatitis, chronic hepatitis, liver cirrhosis, and fulminant hepatitis. It is said to be very difficult to treat these liver diseases. Namely, currently available methods for the treatment such as treatments with pharmaceuticals e.g. liver protective agents such as various vitamins, saccharides, amino acids, glutathione, glycyrrhizin, liver hydrolyzates or adrenocortical hormones; cholagogues; immunomodulators; or antiviral substances against viral hepatitis, are all nothing more than symptomatic treatments, and they are not adequately effective for the treatment of the existing liver damages.

It has recently been reported that 1,3-dithiole derivatives represented by Malotilate as identified below, are effective for the treatment of liver damages (see Japanese Examined Patent Publications No. 18,576/1981, No. 18,577/1981 and No. 18,578/1981).

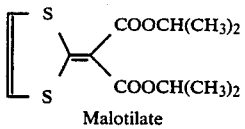

Malotilate

As a result of extensive researches, the present inventors have found that certain novel 1,3-dithiole derivatives represented by the after-mentioned formula I, had exhibited excellent activities for the treatment of a wide spectrum of liver damages, which had been comparable or superior to the above-mentioned conventional 1,3-dithiole derivatives. The present invention has been accomplished on the basis of this discovery.

Namely, the present invention provides a 1,3-dithiole derivative having the formula:

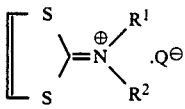 (I)

wherein each of $R^1$ and $R^2$ is an alkyl, cycloalkyl, lower alkenyl, lower alkynyl, aryl or aralkyl group which may be substituted by halogen, hydroxyl, cyano, lower alkyl, lower alkoxy, lower alkylthio, lower alkoxycarbonyl, or

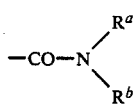

wherein each of $R^a$ and $R^b$ is a hydrogen atom, a lower alkyl group, a cycloalkyl group, a lower alkenyl group, a lower alkynyl group, an aryl group or an aralkyl group, or $R^1$ and $R^2$ together form an alkylene or alkenylene group having from 3 to 6 carbon atoms, which may contain a cycloalkylene group, an o-phenylene group or a hetero atom selected from the group consisting of an oxygen atom, a sulfur atom and a nitrogen atom which may have a substitutent selected from the group consisting of a lower alkyl group, a lower alkenyl group, a lower alkynyl group, a lower alkoxycarbonyl group, a hydroxy-substituted lower alkyl group, an aryl group and an aralkyl group, and said alkylene or alkenylene group may be substituted by one or two substituents selected from the group consisting of a lower alkyl group, an aryl group, an aralkyl group, a hydroxyl group, a lower alkoxy group, a lower alkylthio group, a hydroxy-substituted lower alkyl group, a cyano group, a carboxyl group, a lower alkoxycarbonyl group, a di-lower alkylamino group, a lower alkanoylamino group and a

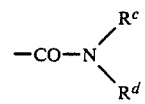

group wherein each of $R^c$ and $R^d$ is a hydrogen atom, a lower alkyl group, an aryl group or an aralkyl group, provided that $R^1$ and $R^2$ are not methyl groups or ethyl groups at the same time, and Q is an acid residue.

The present invention also provides a process for producing the 1,3-dithiole derivative of the formula I, which comprises reacting a dithiolium salt having the formula:

 (II)

wherein R is a lower alkyl group or an aralkyl group, and Q is as defined above, with an amine having the formula:

 (III)

wherein $R^1$ and $R^2$ are as defined above.

Further, the present invention provides a pharmaceutical composition for treating liver diseases, which comprises an effective amount of a 1,3-dithiole derivative of the formula I as defined in claim 1 and a pharmaceutically acceptable carrier or diluent.

Now, the present invention will be described in detail with reference to the preferred embodiments.

Referring to the definitions of $R^1$ and $R^2$ in the formula I, the alkyl group includes $C_1$-$C_{20}$ alkyl such as methyl, ethyl, n-propyl, isopropyl, n-butyl, isobutyl, n-hexyl, n-octyl, n-decyl, n-dodecyl, n-hexadecyl, n-octadecyl and n-icosanyl.

In this specification, the term "lower" means a straight or branched carbon chain having from 1 to 6 carbon atoms unless otherwise specified. Accordingly, the lower alkyl group includes methyl, ethyl, n-propyl, isopropyl, n-butyl, isobutyl and n-hexyl; the lower alkenyl group includes 1-propenyl, allyl, 2-methyl-2-propenyl and 2-butenyl; the lower alkynyl group includes propargyl and 2-butynyl; the lower alkoxy group includes methoxy and ethoxy; the lower alkylthio group includes methylthio and ethylthio; and the lower alkoxycarbonyl group includes methoxycarbonyl, ethoxycarbonyl, n-propoxycarbonyl, isopropoxycarbonyl and tert-butoxycarbonyl.

Likewise, the cycloalkyl group includes cyclopropyl, cyclopentyl and cyclohexyl; the aryl group includes phenyl, pyridyl and naphthyl; and the aralkyl group includes benzyl, phenethyl and naphthylmethyl. The aryl group may have substituents such as halogen, hydroxyl, lower alkyl, lower alkoxy, lower alkoxycarbonyl.

The

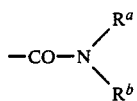

group includes carbamoyl, N-methylcarbamoyl, N,N-dimethylcarbamoyl, N-ethylcarbamoyl and N-phenylcarbamoyl.

Further, $R^1$ and $R^2$ may together form an alkylene or alkenylene group having from 3 to 6 carbon atoms, such as $-(CH_2)_4-$, $-(CH_2)_5-$, $-(CH_2)_6-$, $-CH_2OCH_2CH_2-$, $-CH_2SCH_2CH_2-$, $-CH_2CH_2SCH_2CH_2-$, $-CH_2CH_2OCH_2CH_2-$, $-CH_2CH_2NHCH_2CH_2-$, $-CH_2CH_2N(Ph)CH_2CH_2-$, $-CH_2CH_2N(CH_2Ph)CH_2CH_2-$, $-CH_2CH_2N(CH_3)CH_2CH_2-$, $-CH_2CH=CHCH_2-$, $-CH_2CH=CHCH_2CH_2-$,

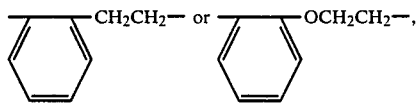

which may be substituted by hydroxyl, cyano, carboxyl, methyl, ethyl, n-propyl, isopropyl, n-butyl, n-pentyl, n-hexyl, phenyl, naphthyl, benzyl, naphthylmethyl, methoxy, ethoxy, methylmercapto, ethylmercapto, hydroxymethyl, 1-hydroxyethyl, methoxycarbonyl, ethoxycarbonyl, isopropoxycarbonyl, dimethylamino, diethylamino, acetylamino, propionylamino, carbamoyl, N-methylcarbamoyl, N,N-dimethylcarbamoyl, N-phenylcarbamoyl or N-benzylcarbamoyl.

Q is an acid residue, e.g. a residue of an inorganic acid such as hydrochloric acid, hydrobromic acid, hydroiodic acid, nitric acid, perchloric acid, borofluoric acid, sulfuric acid or phosphoric acid, or a residue of an organic acid such as oxalic acid, tartaric acid, citric acid, methanesulfonic acid or p-toluenesulfonic acid. Namely, such specific acid residues include Cl, Br, I, $HSO_4$, $ClO_4$, $NO_3$, $CH_3SO_3$, $BF_4$ and HOOC-COO.

Specific examples of the compounds of the formula I of the present invention will be given below:

N-(1,3-dithiol-2-ylidene)-N-methyl-N-ethoxycarbonylmethylammonium perchlorate (Compound No. 1)
N-(1,3-dithiol-2-ylidene)-N-methyl-N-ethoxycarbonylmethylammonium chloride (Compound No. 2)
N-(1,3-dithiol-2-ylidene)-N-methyl-N-(N'-methylcarbamoylmethyl)ammonium perchlorate (Compound No. 3)
N-(1,3-dithiol-2-ylidene)-N-methyl-N-(2-cyanoethyl)ammonium iodide (Compound No. 4)
N-(1,3-dithiol-2-ylidene)-N-methyl-N-(2-phenyl-1-methoxycarbonylethyl)ammonium iodide (Compound No. 5)
N-(1,3-dithiol-2-ylidene)-N-methyl-N-(3-methylthio-1-ethoxycarbonylpropyl)ammonium perchlorate (Compound No. 6)
N-(1,3-dithiol-2-ylidene)-N-methyl-N-cyclohexylammonium perchlorate (Compound No. 7)
N-(1,3-dithiol-2-ylidene)-N-methyl-N-phenylammonium perchlorate (Compound No. 8)
N-(1,3-dithiol-2-ylidene)-N-methyl-N-(m-tolyl)ammonium perchlorate (Compound No. 9)
N-(1,3-dithiol-2-ylidene)-N-methyl-N-benzylammonium perchlorate (Compound No. 10)
N-(1,3-dithiol-2-ylidene)-N-ethyl-N-(2-ethoxyethyl)ammonium perchlorate (Compound No. 11)
N-(1,3-dithiol-2-ylidene)-N,N-diallylammonium perchlorate (Compound No. 12)
N-(1,3-dithiol-2-ylidene)-N,N-diisopropylammonium perchlorate (Compound No. 13)
N-(1,3-dithiol-2-ylidene)-N,N-di(n-hexyl)ammonium perchlorate (Compound No. 14)
N-(1,3-dithiol-2-ylidene)-N,N-diphenylammonium perchlorate (Compound No. 15)
N-(1,3-dithiol-2-ylidene)-N,N-dibenzylammonium perchlorate (Compound No. 16)
N-(1,3-dithiol-2-ylidene)-N-methyl-N-(1,2-dimethoxycarbonylethyl)ammonium perchlorate (Compound No. 17)
N-(1,3-dithiol-2-ylidene)-N-methyl-N-(3-methyl-1-isopropoxycarbonylbutyl)ammonium perchlorate (Compound No. 18)
N-(1,3-dithiol-2-ylidene)-N-ethyl-N-(n-butyl)ammonium perchlorate (Compound No. 19)
N-(1,3-dithiol-2-ylidene)-N,N-di(n-octyl)ammonium perchlorate (Compound No. 20)
N-(1,3-dithiol-2-ylidene)-N,N-di(n-decyl)ammonium perchlorate (Compound No. 21)
N-(1,3-dithiol-2-ylidene)-N-methyl-N-(4-chlorophenyl)ammonium perchlorate (Compound No. 22)
N-(1,3-dithiol-2-ylidene)-N,N-di(n-butyl)ammonium perchlorate (Compound No. 23)
N-(1,3-dithiol-2-ylidene)-N,N-di(2-hydroxyethyl)ammonium perchlorate (Compound No. 24)
N-(1,3-dithiol-2-ylidene)-N-methyl-N-propargyl ammonium iodide (Compound No. 25)
4-(1,3-dithiol-2-ylidene)morpholinium perchlorate (Compound No. 26)
4-(1,3-dithiol-2-ylidene)morpholinium chloride (Compound No. 27)
4-(1,3-dithiol-2-ylidene)morpholinium bromide (Compound No. 28)
4-(1,3-dithiol-2-ylidene)morpholinium iodide (Compound No. 29)
4-(1,3-dithiol-2-ylidene)morpholinium hydrogensulfate (Compound No. 30)
1-(1,3-dithiol-2-ylidene)-4-methylpiperazinium perchlorate (Compound No. 31)
1-(1,3-dithiol-2-ylidene)-4-phenylpiperazinium perchlorate (Compound No. 32)
1-(1,3-dithiol-2-ylidene)-4-benzylpiperazinium perchlorate (Compound No. 33)
1-(1,3-dithiol-2-ylidene)piperidinium perchlorate (Compound No. 34)
1-(1,3-dithiol-2-ylidene)pyrrolidinium perchlorate (Compound No. 35)
3-(1,3-dithiol-2-ylidene)thiazolidinium perchlorate (Compound No. 36)

1-(1,3-dithiol-2-ylidene)hexahydroazepinium perchlorate (Compound No. 37)
1-(1,3-dithiol-2-ylidene)-4-ethoxycarbonylpiperazinium perchlorate (Compound No. 38)
4-(1,3-dithiol-2-ylidene)thiomorpholinium perchlorate (Compound No. 39)
1-(1,3-dithiol-2-ylidene)-4-(2-hydroxyethyl)-piperazinium perchlorate (Compound No. 40)
1-(1,3-dithiol-2-ylidene)-2-ethoxycarbonyl pyrrolidinium perchlorate (Compound No. 41)
1-(1,3-dithiol-2-ylidene)-2-ethoxycarbonyl pyrrolidinium chloride (Compound No. 42)
1-(1,3-dithiol-2-ylidene)-2-carboxypyrrolidinium perchlorate (Compound No. 43)
1-(1,3-dithiol-2-ylidene)-2-carbamoylpyrrolidinium iodide (Compound No. 44)
1-(1,3-dithiol-2-ylidene)-2-(n-hexyl)pyrrolidinium perchlorate (Compound No. 45)
1-(1,3-dithiol-2-ylidene)-2-phenylpyrrolidinium perchlorate (Compound No. 46)
1-(1,3-dithiol-2-ylidene)-3-hydroxymethylpyrrolidinium perchlorate (Compound No. 47)
1-(1,3-dithiol-2-ylidene)-2-ethoxycarbonyl-4-hydroxypyrrolidinium perchlorate (Compound No. 48)
1-(1,3-dithiol-2-ylidene)-2,5-dimethylpyrrolidinium perchlorate (Compound No. 49)
3-(1,3-dithiol-2-ylidene)-4-ethoxycarbonylthiazolidinium perchlorate (Compound No. 50)
1-(1,3-dithiol-2-ylidene)-2-methylpiperidinium perchlorate (Compound No. 51)
1-(1,3-dithiol-2-ylidene)-3-methylpiperidinium perchlorate (Compound No. 52)
1-(1,3-dithiol-2-ylidene)-4-methylpiperidinium perchlorate (Compound No. 53)
1-(1,3-dithiol-2-ylidene)-2-ethoxycarbonylpiperidinium perchlorate (Compound No. 54)
1-(1,3-dithiol-2-ylidene)-3-ethoxycarbonylpiperidinium iodide (Compound No. 55)
1-(1,3-dithiol-2-ylidene)-4-ethoxycarbonylpiperidinium perchlorate (Compound No. 56)
1-(1,3-dithiol-2-ylidene)-4-carboxypiperidinium perchlorate (Compound No. 57)
1-(1,3-dithiol-2-ylidene)-4-carbamoylpiperidinium iodide (Compound No. 58)
1-(1,3-dithiol-2-ylidene)-4-cyanopiperidinium perchlorate (Compound No. 59)
1-(1,3-dithiol-2-ylidene)-4-hydroxypiperidinium perchlorate (Compound No. 60)
1-(1,3-dithiol-2-ylidene)-4-methoxypiperidinium perchlorate (Compound No. 61)
1-(1,3-dithiol-2-ylidene)-4-methylthiopiperidinium perchlorate (Compound No. 62)
1-(1,3-dithiol-2-ylidene)-4-acetamidopiperidinium perchlorate (Compound No. 63)
1-(1,3-dithiol-2-ylidene)-4-(N',N'-dimethylamino)-piperidinium perchlorate (Compound No. 64)
1-(1,3-dithiol-2-ylidene)-3-phenylpiperidinium perchlorate (Compound No. 65)
1-(1,3-dithiol-2-ylidene)-4-benzylpiperidinium perchlorate (Compound No. 66)
1-(1,3-dithiol-2-ylidene)-3,5-dimethylpiperidinium iodide (Compound No. 67)
1-(1,3-dithiol-2-ylidene)-3-ethoxycarbonyl-6-methylpiperidinium perchlorate (Compound No. 68)
1-(1,3-dithiol-2-ylidene)indolinium perchlorate (Compound No. 69)
1-(1,3-dithiol-2-ylidene)benzmorpholinium perchlorate (Compound No. 70)
4-(1,3-dithiol-2-ylidene)-1,2-dimethylpiperadinium perchlorate (Compound No. 71)

However, the present invention is not restricted to these specific examples. Further, some of the compounds of the formula I may exist in the form of optically active substances or racemic modifications. The present invention covers such compounds.

The compound of the formula I of the present invention may be prepared by reacting a dithiolium salt of the formula II with an amine of the formula III.

The dithiolium salt of the formula II is a known compound, and may be prepared by a method disclosed in literature, for instance, by alkylating 1,3-dithiol-2-thione with dimethyl sulfate, methyl iodide or ethyl iodide, or by aralkylating 1,3-dithiol-2-thione with benzyl chloride or phenethyl chloride [Chem. Ber. 98, 1365 (1965)].

The amine of the formula III includes sarcosine ethyl ester, sarcosine N-methylamide, N-methyl(2-cyanoethyl)amine, N-methylphenylalanine ethyl ester, N-methylmethionine ethyl ester, N-methylcyclohexylamine, N-methylaniline, N-methyl-m-toluidine, N-methyl-4-chloroaniline, N-methylbenzylamine, N,N-di(2-hydroxyethyl)amine, N-ethyl-(2-ethoxyethyl)amine, N,N-diallylamine, N-methylpropargylamine, N,N-diisopropylamine, N-methylethylamine, N,N-di(n-butyl)amine, N,N-di(n-hexyl)amine, N,N-di(n-octyl)amine, N,N-di(n-decyl)amine, N,N-diphenylamine, N,N-dibenzylamine, N-methylaspartic acid methyl ester, N-methylleucine isopropyl ester, pyrrolidine, piperidine, hexahydroazepine, oxazolidine, thiazolidine, thiomorpholine, morpholine, piperazine, N-phenylpiperazine, N-benzylpiperazine, N-methylpiperazine, N-ethoxycarbonylpiperazine, N-(2-hydroxyethyl)piperazine, proline, proline ethyl ester, proline amide, 2-(n-hexyl)pyrrolidine, 2-phenylpyrrolidine, 3-hydroxymethylpyrrolidine, 4-hydroxyproline ethyl ester, 2,5-dimethylpyrrolidine, thiazolidine-4-carboxylic acid ethyl ester, α-pipecoline, β-pipecoline, γ-pipecoline, pipecolic acid ethyl ester, nipecotic acid ethyl ester, isonipecotic acid, isonipecotic acid ethyl ester, isonipecotic acid amide, isonipecotinonitrile, 4-hydroxypiperidine, 4-methoxypiperidine, 4-methylthiopiperidine, 4-acetamidopiperidine, N',N'-dimethylaminopiperidine, 3-phenylpiperidine, 4-benzylpiperidine, 3,5-dimethylpiperidine, 6-methylnipecotic acid ethyl ester, indoline, 1,2-dimethylpiperazine, benzmorpholine and 1,2-dimethylpiperazine. These amines are commercially available, or may be readily obtainable by a method disclosed in literature or by a similar method.

For the production of the compounds of the present invention, the reaction of the dithiolium salt of the formula II with the amine of the formula III is conducted usually in an inert solvent which does not adversely affect the reaction. As such an inert solvent, water, tetrahydrofuran, dioxane, an alcohol, acetone, ethyl acetate, chloroform, benzene, acetonitrile, dimethylsulfoxide, dimethylformamide or a mixture thereof may be employed. The reaction is conducted usually in a temperature range of from −20° C. to the boiling point of the solvent. However, for the purpose of controlling the reaction rate, the reaction may be conducted at a temperature higher or lower than the above range.

The compounds of the formula I formed by the above reaction may be isolated in accordance with a conventional method such as crystallization from the reaction solution or solvent extraction. The product may be further purified by recrystallization or column chromatography as the case requires.

The compounds of the present invention are usually in the form of an acid addition salt with the acid residue represented by Q. This acid residue may be substituted by another acid. For instance, it is possible to obtain another acid addition salt by recrystallization in the presence of a substantial amount of another acid or by passing the product through a column of a basic ion exchange resin in the form of a salt with another acid.

When the compound of the present invention is to be used as a drug for treating the liver diseases, its dose is usually from 0.1 to 100 mg a day per kg of the body weight in the case of oral administration, and from 0.01 to 25 mg a day per kg of the body weight in the case of parenteral administration, although it may vary depending upon the body weight, age, sex or health condition of the patient, the manner of administration or the degree of disease.

The compound of the present invention may be formulated into various forms such as tablets, granules, powders, suspensions, capsules, solutions for injection or isotonic solutions in accordance with the conventional methods which are commonly used in the technical fields for pharmaceutical formulations.

For the production of solid formulations for oral administration, the active ingredient is incorporated with a vehicle and necessary additives such as a condensing agent, a disintegrator, a lubricant, a coloring agent, or a taste- or odor-controlling agent, and then the mixture is formed into tablets, coated tablets, granules, powders or capsules by conventional methods.

For the preparation of injection solutions, the active ingredient is incorporated with a pH controlling agent, a buffer, a suspending agent, a dissolving agent, a stabilizer, an isotonic agent, a storage assistant, etc., if required, and the mixture is formulated into hypodermic, intramuscular or intravenous injection solutions by conventional methods.

The compounds of the present invention effectively prevent the elevation of GPT (glutamic-pyruvic transaminase) activity and the retention rate of BSP (sodium sulfobromophthalein) in the plasma of an animal liver injury model induced by carbon tetrachloride, and thus exhibit remarkable effects for preventing the liver injury. As will be evident from the pharmacological tests given hereinafter, their activities are far superior to the conventional 1,3-dithiole derivatives represented by Malotilate and their safety range is wide, in the animal liver injury model.

PHARMACOLOGICAL TESTS

1. Protective Effect on Acute Liver Injury Induced by Carbon Tetrachloride

A test compound was dissolved or suspended in olive oil and administered orally to mice (ddY mice, ♂, 23±2 g, n=5). After 6 hours, carbon tetrachloride (0.05 ml/kg) was administered orally. 24 Hours after the administration of carbon tetrachloride, BSP (sodium sulfobromophthalein; 75 mg/kg) was administered intravenously. Thirty minutes later, the cardiac blood was collected, and GPT (glutamic-pyruvic transaminase) activity and the retention rate of BSP in the plasma were measured.

As shown in Tables 1 to 3, the compounds of the present invention showed remarkable effects for preventing the liver injury, which are superior to Malotilate as the comparative compound.

TABLE 1

| Compound | Dose (mg/kg) | GPT activity (Karmen units) | Retained BSP (μg/ml) |
|---|---|---|---|
| 1 | 1 | 3280 ± 399 | 53.2 ± 11.4 |
|   | 5 | 183 ± 74 | 18.4 ± 1.3 |
| 2 | 1 | 3190 ± 412 | 57.4 ± 12.3 |
|   | 5 | 192 ± 84 | 17.1 ± 1.4 |
| 3 | 1 | 3740 ± 430 | 67.1 ± 14.3 |
|   | 5 | 541 ± 101 | 27.1 ± 10.1 |
| 4 | 1 | 2535 ± 158 | 42.6 ± 2.3 |
|   | 5 | 543 ± 92 | 29.4 ± 11.1 |
| 7 | 1 | 4920 ± 670 | 120.1 ± 17.1 |
|   | 5 | 1400 ± 77 | 57.1 ± 5.1 |
| 8 | 1 | 2394 ± 193 | 39.3 ± 10.7 |
|   | 5 | 117 ± 28 | 11.6 ± 1.5 |
| 9 | 1 | 2250 ± 325 | 73.1 ± 14.7 |
|   | 5 | 191 ± 71 | 21.4 ± 2.1 |
| 10 | 1 | 1865 ± 106 | 29.5 ± 6.0 |
|   | 5 | 108 ± 27 | 16.6 ± 1.6 |
| 12 | 1 | 5438 ± 401 | 109.3 ± 14.8 |
|   | 5 | 1241 ± 103 | 25.4 ± 5.0 |
| 16 | 1 | 4121 ± 311 | 107.4 ± 13.9 |
|   | 5 | 1017 ± 37 | 21.8 ± 6.0 |
| 17 | 1 | 4760 ± 298 | 135 ± 8.9 |
|   | 5 | 3883 ± 324 | 86 ± 11.1 |
| 18 | 1 | 4100 ± 615 | 106.9 ± 17.5 |
|   | 5 | 3250 ± 365 | 44.1 ± 5.2 |
| Malotilate | 10 | 3480 ± 608 | 79.4 ± 21.4 |
|   | 50 | 168 ± 31 | 18.4 ± 2.0 |
| CCl4 alone | — | 6410 ± 478 | 125.1 ± 20.0 |
| No treatment | — | 17 ± 1 | 15.1 ± 1.0 |

TABLE 2

| Compound | Dose (mg/kg) | GPT activity (Karmen units) | Retained BSP (μg/ml) |
|---|---|---|---|
| 26 | 1 | 483 ± 178 | 21.6 ± 2.7 |
|   | 5 | 113 ± 32 | 13.8 ± 2.5 |
| 31 | 1 | 523 ± 111 | 20.3 ± 3.4 |
|   | 5 | 148 ± 51 | 12.6 ± 0.6 |
| 34 | 1 | 512 ± 205 | 26.5 ± 8.0 |
|   | 5 | 116 ± 39 | 15.6 ± 3.0 |
| 35 | 1 | 4239 ± 816 | 101.2 ± 22.6 |
|   | 5 | 2472 ± 820 | 35.8 ± 12.4 |
| Malotilate | 10 | 2356 ± 702 | 76.2 ± 20.7 |
|   | 50 | 123 ± 23 | 16.1 ± 2.0 |
| CCl4 alone | — | 5386 ± 489 | 121.4 ± 21.1 |
| No treatment | — | 15 ± 1 | 15.7 ± 1.0 |

TABLE 3

| Compound | Dose (mg/kg) | GPT activity (Karmen units) | Retained BSP (μg/ml) |
|---|---|---|---|
| 41 | 1 | 405 ± 73 | 26.5 ± 3.1 |
|   | 5 | 165 ± 21 | 17.9 ± 2.0 |
| 42 | 1 | 1673 ± 214 | 53.1 ± 6.3 |
|   | 5 | 231 ± 43 | 21.4 ± 3.5 |
| 44 | 1 | 6311 ± 867 | 134.7 ± 21.7 |
|   | 5 | 5213 ± 716 | 119.4 ± 11.8 |
| 45 | 1 | 4264 ± 521 | 110 ± 20.5 |
|   | 5 | 1072 ± 282 | 76 ± 6.3 |
| 46 | 1 | 3978 ± 627 | 101 ± 17.4 |
|   | 5 | 1040 ± 121 | 69 ± 7.1 |
| 52 | 1 | 2391 ± 325 | 87.1 ± 13.4 |
|   | 5 | 138 ± 18 | 17.8 ± 4.9 |
| 53 | 1 | 1843 ± 162 | 70.0 ± 19.3 |
|   | 5 | 193 ± 81 | 16.9 ± 3.1 |
| 55 | 1 | 2981 ± 169 | 83.9 ± 14.1 |
|   | 5 | 361 ± 49 | 18.3 ± 4.4 |
| 56 | 1 | 2713 ± 147 | 76.6 ± 13.1 |
|   | 5 | 216 ± 32 | 21.0 ± 13.4 |
| 57 | 1 | 3735 ± 374 | 101.1 ± 20.0 |
|   | 5 | 2922 ± 247 | 90.1 ± 14.7 |
| 58 | 1 | 3266 ± 245 | 98.1 ± 21.0 |
|   | 5 | 1151 ± 181 | 41.5 ± 7.1 |
| 59 | 1 | 2991 ± 382 | 110.1 ± 27.3 |
|   | 5 | 763 ± 118 | 49.1 ± 8.1 |
| 60 | 1 | 1321 ± 197 | 63.4 ± 10.9 |
|   | 5 | 131 ± 10 | 19.1 ± 2.1 |
| 67 | 1 | 2718 ± 431 | 111.4 ± 17.1 |

TABLE 3-continued

| Compound | Dose (mg/kg) | GPT activity (Karmen units) | Retained BSP (µg/ml) |
|---|---|---|---|
| Malotilate | 5 | 372 ± 27 | 21.3 ± 4.0 |
|  | 10 | 2941 ± 501 | 87.4 ± 21.8 |
|  | 50 | 298 ± 40 | 17.4 ± 2.0 |
| CCl$_4$ alone | — | 5386 ± 489 | 121.4 ± 11.0 |
| No treatment | — | 15 ± 1 | 15.7 ± 1.0 |

2. Actute toxicity test

A test compound was suspended in olive oil and administered orally to mice (ddY mice, ♂, 23±2 g, n=5 or 6). The actute toxicity value (LD$_{50}$) was determined from the mortality 1 week after the administration.

Compounds No. 2, No. 31, No. 41, No. 55 and No. 56 of the present invention showed extremely low toxicity and their LD$_{50}$ values were at least 1500 mg/kg.

Now, the present invention will be described in detail with reference to Examples. However, it should be understood that the present invention is by no means restricted to these specific Examples.

EXAMPLE 1

To 30 ml of tetrahydrofuran, 1.4 g of N-methylglycine ethyl ester was dissolved, and 2.0 g of 2-methylthio-1,3-dithiolium perchlorate was gradually added thereto under stirring at room temperature. The mixture was stirred at room temperature for 1 hour, and the precipitated crystals were collected by filtration and recrystallized from acetone-ethyl ether, whereby 1.7 g (yield: 67%) of N-(1,3-dithiol-2-ylidene)-N-methyl-N-ethoxycarbonylmethylammonium perchlorate (Compound No. 1) was obtained as crystals having a melting point of from 104° to 105° C.

IR $\nu_{max}^{KBr}$cm$^{-1}$: 3100, 1740, 1580, 1420, 1380, 1240, 1080.

NMR(d$_6$—DMSO)δ: 1.21(3H, t, J=7 Hz), 3.53(3H, s), 4.24(2H, q J=7 Hz), 4.80(2H, s), 7.81(2H, s).

EXAMPLES 2 to 11

The following compounds were prepared in the same manner as in Example 1.

EXAMPLE 2

N-(1,3-dithiol-2-ylidene)-N-methyl-N-(N'-methylcarbamoylmethyl)ammonium perchlorate (Compound No. 3)

mp: 140°-141° C. (recrystallized from methanol).

IR $\nu_{max}^{KBr}$cm$^{-1}$: 3250, 3075, 1660, 1570, 1425, 1080, 710.

NMR(d$_6$—DMSO)δ: 2.65(2H, d J=8 Hz), 3.46(3H, s), 4.54(2H, s), 7.66(2H, s), 8.25(1H, br, s).

EXAMPLE 3

N-(1,3-dithiol-2-ylidene)-N-methyl-N-cyclohexylammonium perchlorate (Compound No. 7)

mp: 123° C. (recrystallized from acetone-ethyl ether).

IR $\nu_{max}^{KBr}$cm$^{-1}$: 3080, 2950, 1560, 1520, 1425, 1090.

NMR(d$_6$—DMSO)δ: 0.81-2.30(10H, m), 3.33(3H, s), 3.73(1H, m), 7.60(2H, s).

EXAMPLE 4

N-(1,3-dithiol-2-ylidene)-N-methyl-N-(m-tolyl) ammonium perchlorate (Compound No. 9)

mp: 200°-201° C. (recrystallized from acetone-ethyl ether).

IR $\nu_{max}^{KBr}$cm$^{-1}$: 3060, 1555, 1510, 1400, 1080.

NMR(d$_6$—DMSO)δ: 2.36(3H, s), 3.74(3H, s), 7.45(2H, s), 7.31-7.80(4H, m).

EXAMPLE 5

N-(1,3-dithiol-2-ylidene)-N-methyl-N-benzylammonium perchlorate (Compound No. 10)

mp: 193°-194° C. (recrystallized from acetone-ethyl ether).

IR $\nu_{max}^{KBr}$cm$^{-1}$: 3070, 1560, 1510, 1450, 1410, 1070.

NMR(d$_6$—DMSO)δ: 3.30(3H, s), 5.10(2H, s), 7.45(5H, s), 7.75(2H, s).

EXAMPLE 6

N-(1,3-dithiol-2-ylidene)-N,N-diallylammonium perchlorate (Compound No. 12)

mp: 76° C. (recrystallized from acetone-ethyl ether).

IR $\nu_{max}^{KBr}$cm$^{-1}$: 3080, 1550, 1515, 1445, 1270, 1240.

NMR(d$_6$—DMSO)δ: 4.44(4H, d J=6 Hz), 5.20-6.25(6H, m), 7.64(2H, s).

EXAMPLE 7

N-(1,3-dithiol-2-ylidene)-N,N-diisopropylammonium perchlorate (Compound No. 13)

mp: 194°-197° C. (recrystallized from acetone-ethyl ether).

IR $\nu_{max}^{KBr}$cm$^{-1}$: 3100, 1560, 1520, 1385, 1360, 1110, 1095, 1070, 830, 690.

NMR(d$_6$—DMSO)δ: 1.42(6H, d J=6.5 Hz), 4.42(2H, m), 7.73(2H, s).

EXAMPLE 8

N-(1,3-dithiol-2-ylidene)-N,N-di(n-hexyl)ammonium perchlorate (Compound No. 14)

mp: 60° C. (recrystallized from ethyl acetateethyl ether).

IR $\nu_{max}^{KBr}$cm$^{-1}$: 3060, 2940, 1560, 1520, 1475, 1150, 1130, 1090.

NMR(d$_6$—DMSO)δ: 0.90(6H, t J=7 Hz), 1.01-2.02(16H, m), 3.80(4H, t J=7 Hz), 7.68(2H, s).

EXAMPLE 9

N-(1,3-dithiol-2-ylidene)-N,N-dibenzylammonium perchlorate (Compound No. 16)

mp: 137°-138° C. (recrystallized from acetone-ethyl ether).

IR $\nu_{max}^{KBr}$cm$^{-1}$: 3050, 1503, 1435, 1425, 1140, 1070.

NMR(d$_6$—DMSO)δ: 5.16(4H, s), 7.34(10H, s), 7.60(2H, s).

EXAMPLE 10

N-(1,3-dithiol-2-ylidene)-N-methyl-N-(1,2-dimethoxycarbonylethyl)ammonium perchlorate (Compound No. 17)

mp: 155°-156° C. (recrystallized from acetone-ethyl ether).

IR $\nu_{max}^{KBr}$cm$^{-1}$: 3100, 2950, 1740, 1725, 1550, 1510, 1330, 1230, 1100, 850, 830.

NMR(d$_6$—DMSO)δ: 3.28(2H, d J=7 Hz), 3.37(3H, s), 3.61(3H, s), 3.72(3H, s), 5.34(1H, t J=7 Hz), 7.78(2H, s).

EXAMPLE 11

N-(1,3-dithiol-2-ylidene)-N-methyl-N-(3-methyl-1-isopropoxycarbonylbutyl)ammonium perchlorate (Compound No. 18)

mp: 110°-112° C. (recrystallized from acetone-ethyl ether).

IR $\nu_{max}^{KBr}$cm$^{-1}$: 1735, 1545, 1405, 1280, 1120.

NMR(d$_6$–DMSO)δ: 0.96(6H, d J=7 Hz), 1.32(3H, d J=7 Hz), 2.01(2H, t J=7 Hz), 2.94(1H, m), 3.51(3H, s), 4.76(1H, t, J=7 Hz), 5.10(1H, m), 7.60(2H, s).

EXAMPLE 12

A solution obtained by dissolving 2.0 g of N-(1,3-dithiol-2-ylidene)-N-methyl-N-ethoxycarbonylmethyl ammonium perchlorate in 100 ml of water, was passed through a column of 200 cc of an anion exchange resin (Dowex 1-X8 hydrochloride-form), and the fraction containing the desired product is concentrated under reduced pressure. The residue was recrystallized from methanol-ethyl ether, whereby 1.4 g (yield: 88%) of N-(1,3-dithiol-2-ylidene)-N-methyl-N-ethoxycarbonylmethyl ammonium chloride (Compound No. 2) was obtained as crystals having a melting point of from 85° to 87° C.

IR $\nu_{max}^{KBr}$cm$^{-1}$: 3400, 2930, 1745, 1570, 1520, 1370, 1220, 1035, 700.

NMR(CD$_3$OD)δ: 1.29(3H, t J=7.2 Hz), 3.51(3H, s), 4.20(2H, q J=7.2 Hz), 4.73(2H, s), 7.68(2H, s).

EXAMPLE 13

To 30 ml of tetrahydrofuran, 0.8 g of N-methyl-(2-cyanoethyl)amine was dissolved, and 2.0 g of 2-methylthio-1,3-dithiolium iodide was gradually added thereto under stirring at room temperature. The mixture was stirred at room temperature for 1 hour, and then the precipitated crystals were collected by filtration and recrystallized from acetone-ethyl ether, whereby 1.8 g (yield: 80%) of 1-(1,3-dithiol-2-ylidene)-N-methyl-N-(2-cyanoethyl)ammonium iodide (Compound No. 4) was obtained as crystals having a melting point of 203° C.

IR $\nu_{max}^{KBr}$cm$^{-1}$: 3070, 2250, 1563, 1520, 1405, 1235, 1112, 830.

NMR(D$_2$O)δ: 3.13(2H, t J=7 Hz), 3.55(3H, s), 4.21(2H, t J=7 Hz), 7.62(2H, s).

EXAMPLE 14

To 100 ml of acetone, 2.2 g of N-methylphenylalanine methyl ester was dissolved, and 2.0 g of 2-methylthio-1,3-dithiolium iodide was gradually added thereto under stirring at room temperature. The mixture was stirred at room temperature for 1 hour, and then concentrated under reduced pressure. The residue was dissolved in water. The aqueous layer was washed with ethyl acetate, and then water was distilled off under reduced pressure, whereby 1.7 g (yield: 52%) of N-(1,3-dithiol-2-ylidene)-N-methyl-N-(2-phenyl-1-methoxycarbonylethyl)ammonium iodide (Compound No. 5) was obtained as oily substance.

IR $\nu_{max}^{KBr}$cm$^{-1}$: 3400, 3060, 2950, 1740, 1550, 1520, 1410, 1270, 1240, 1100, 750.

NMR(d$_6$–DMSO)δ: 3.42(3H, s), 3.46(2H, m), 3.81(3H, s), 5.44(1H, m), 7.34(5H, m), 7.71(2H, m).

EXAMPLE 15

To 100 ml of acetone, 2.0 g of 2-methylthio-1,3-dithiolium perchlorate was dissolved, and 50 ml of an ethyl ether solution containing 2.3 g of N-methyl methionine ethyl ester was gradually added thereto under stirring at room temperature. The mixture was stirred at room temperature for 6 hours, and then the solvent was distilled off. The residue was washed with ethyl acetate, whereby 7 g (yield: 54%) of N-(1,3-dithiol-2-ylidene)-N-methyl-N-(3-methylthio-1-ethoxycarbonylpropyl)ammonium perchlorate (Compound No. 6) was obtained as oily substance.

IR $\nu_{max}^{neat}$cm$^{-1}$: 3090, 2980, 1740, 1560, 1515, 1245, 1100.

NMR(CD$_3$OD)δ: 1.28(3H, t J=7 Hz), 2.08(3H, s), 2.40–3.01(4H, m), 3.47(3H, s), 4.26(2H, q J=7 Hz), 5.10(1H, t J=6 Hz), 7.70(2H, s).

EXAMPLE 16

To 2 ml of dimethylformamide, 2.0 g of 2-methylthio-1,3-dithiolium perchlorate was suspended, and 1.1 ml of N-methylaniline was gradually added thereto under stirring at room temperature. The mixture was stirred at room temperature for 1 hour, and then after an addition of 30 ml of ethyl acetate, the precipitated crystals were collected by filtration. The product was recrystallized from acetone, whereby 1.7 g (yield: 69%) of N-(1,3-dithiol-2-ylidene)-N-methyl-N-phenylammonium perchlorate (Compound No. 8) was obtained as crystals having a melting point of 169° C.

IR $\nu_{max}^{KBr}$cm$^{-1}$: 3100, 1550, 1510, 1495, 1400, 1080.

NMR(d$_6$–DMSO)δ: 3.31(3H, s), 7.72(7H, s).

EXAMPLES 17 and 18

The following compounds were prepared in the same manner as in Example 16.

EXAMPLE 17

N-(1,3-dithiol-2-ylidene)-N-ethyl-N-(2-ethoxyethyl)ammonium perchlorate (Compound No. 11)

Oily substance.

IR $\nu_{max}^{neat}$cm$^{-1}$: 3400, 2980, 1560, 1470, 1450, 1100.

NMR(CDCl$_3$)δ: 1.21(3H, t J=7 Hz), 1.47(3H, t J=7 Hz), 3.06–4.23(8H, m), 7.50(2H, s).

EXAMPLE 18

N-(1,3-dithiol-2-ylidene)-N,N-diphenylammonium perchlorate (Compound No. 15)

mp: 231°–232° C. (recrystallized from acetone-ethyl ether).

IR $\nu_{max}^{KBr}$cm$^{-1}$: 3050, 1500, 1460, 1450, 1090, 830.

NMR(d$_6$–DMSO)δ: 7.71(2H, s), 7.34–8.20(10H, m).

EXAMPLES 19 TO 22

The following compounds were prepared in the same manner as in Example 1.

EXAMPLE 19

N-(1,3-dithiol-2-ylidene)-N-ethyl-N-(n-butyl)ammonium perchlorate (Compound No. 19)

mp: 77°–78° C. (recrystallized from ethyl acetateethyl ether).

IR $\nu_{max}^{KBr}$cm$^{-1}$: 3100, 2950, 1570, 1470, 1120, 1090.

NMR(CD$_3$OD)δ: 1.0(3H, t), 1.0–2.1(4H, m), 1.4(3H, t), 3.8(2H, t), 3.85(2H, q), 7.55(2H, s).

EXAMPLE 20

N-(1,3-dithiol-2-ylidene)-N,N-di(n-octyl)ammonium perchlorate (Compound No. 20)

mp: 48°–49° C. (recrystallized from ethyl acetateethyl ether).

IR $\nu_{max}^{KBr}$cm$^{-1}$: 2900, 2850, 1550, 1460, 1140, 1080.

NMR(CD$_3$OD)δ: 0.7–2.1(30H, m), 3.85(4H, t), 7.6(2H, s).

EXAMPLE 21

N-(1,3-dithiol-2-ylidene)-N,N-di(n-decyl)ammonium perchlorate (Compound No. 21)

mp: 43.5°–44.5° C. (recrystallized from ethyl acetate-ethyl ether).
IR $\nu_{max}^{KBr}$cm$^{-1}$: 2950, 2870, 1570, 1480, 1150, 1090.
NMR(CD$_3$OD)δ: 0.7–2.1(38H, m), 3.85(4H, t), 7.55(2H, s).

EXAMPLE 22

N-(1,3-dithiol-2-ylidene)-N-methyl-N-(4-chlorophenyl)ammonium perchlorate (Compound No. 22)
mp: 157°–159° C. (recrystallized from acetone-ethyl ether).
IR $\nu_{max}^{KBr}$cm$^{-1}$: 3100, 1552, 1510, 1445, 1080.
NMR(d$_6$–DMSO)δ: 3.4(3H, s), 7.45(2H, s), 7.5(2H, d J=7.5 Hz), 7.95(2H, d J=7.5 Hz).

EXAMPLE 23

To 10 ml of tetrahydrofuran, 2.0 g of 2-methylthio-1,3-dithiolium perchlorate was suspended, and 0.75 ml of dibutylamine was dropwise added over a period of 5 minutes. The mixture was stirred at room temperature for 30 minutes, and the solvent was distilled off under reduced pressure. The residue was dissolved in a mixture of acetone-ethyl ether, and cooled to −70° C. in a cooling medium, whereupon crystals precipitated. The crystals were collected by decantation under cooled condition, and purified by liquid chromatography (column: Senshu pack, Senshu ODS-5301, mobile phase: methanol/water=50/50), whereby 0.20 g (yield: 75%) of N-(1,3-dithiol-2-ylidene)-N,N-di(n-butyl)ammonium perchlorate was obtained as oily substance. (Compound No. 23)
IR $\nu_{max}^{neat}$cm$^{-1}$: 3090, 2970, 1570, 1470, 1180, 1100.
NMR(CD$_3$OD)δ: 1.0(3H, t), 1.2–2.1(8H, m), 3.8(4H, t), 7.55(2H, s).

EXAMPLE 24

The following compound was prepared in the same manner as in Example 23.
N-(1,3-dithiol-2-ylidene)-N,N-di(2-hydroxyethyl)ammonium perchlorate (Compound No. 24)
Oily substance.
IR $\nu_{max}^{neat}$cm$^{-1}$: 3508, 2956, 1562, 1522, 1450, 1096, 626.
NMR(d$_6$–DMSO)δ: 3.7–4.1(8H, m), 4.92(2H, br. s), 7.6(2H, s).

EXAMPLE 25

The following compound was prepared in the same manner as in Example 13.
N-(1,3-dithiol-2-ylidene)-N-methyl-N-propargyl ammonium iodide (Compound No. 25)
mp: 174°–175° C. (recrystallized from ethanol).
IR $\nu_{max}^{KBr}$cm$^{-1}$: 3180, 2112, 1500, 1420, 1400, 1222.
NMR(d$_6$–DMSO)δ: 3.55(3H, s), 3.72(1H, t J=3 Hz), 4.75(2H, d J=2 Hz), 7.80(3H, s).

EXAMPLE 26

To 20 ml of tetrahydrofuran, 1.0 ml of morpholine was dissolved, and 2.5 g of 2-methylthio-1,3-dithiolium perchlorate was gradually added thereto under stirring at room temperature. The mixture was stirred at room temperature for 1 hour, and then the precipitated crystals were collected by filtration and recrystallized from ethanol, whereby 2.4 g (yield: 83.3%) of 4-(1,3-dithiol-2-ylidene)morpholinium perchlorate (Compound No. 26) was obtained as crystals having a melting point of from 177° to 178° C.
IR $\nu_{max}^{KBr}$cm$^{-1}$: 3500, 3100, 1570, 1520, 1440, 1270.
NMR(d$_6$–DMSO)δ: 7.7(2H, s), 3.8(8H, s).

EXAMPLE 27

A solution obtained by dissolving 1.0 g of 4-(1,3-dithiol-2-ylidene)morpholinium perchlorate in 50 ml of water, was passed through a column of 100 cc of an anion exchange resin (Dowex 1-X8 hydrochloride-form), and the fraction containing the desired product was concentrated under reduced pressure. The residue was recrystallized from methanol-ethyl ether, whereby 710 mg (91.5%) of 4-(1,3-dithiol-2-ylidene)morpholinium chloride (Compound No. 27) was obtained as crystals having a melting point of from 272° to 274° C.
IR $\nu_{max}^{KBr}$cm$^{-1}$: 3070, 1570, 1510, 1440, 1280.
NMR(CD$_3$OD)δ: 7.7(2H, s), 3.8(8H, s).

EXAMPLE 28

1.0 g of morpholine and 2.3 g of 2-methyl-1,3-dithiolium bromide were treated in the same manner as in Example 26, and the product was recrystallized from ethanol, whereby 2.2 g (yield: 86.6%) of 4-(1,3-dithiol-2-ylidene)morpholinium bromide (Compound No. 28) was obtained as crystals having a melting point of 274° to 276° C.
IR $\nu_{max}^{KBr}$cm$^{-1}$: 3070, 2890, 1570, 1510, 1440.
NMR(d$_6$–DMSO)δ: 7.7(2H, s), 3.8(8H, s).

EXAMPLE 29

1.0 g of morpholine and 2.8 g of 2-methyl-1,3-dithiolium iodide were treated in the same manner as in Example 26, and the product was recrystallized from ethanol, whereby 2.4 g (yield: 79.7%) of 4-(1,3-dithiol-2-ylidene)morpholinium iodide (Compound No. 29) was obtained as crystals having a melting point of from 257° to 258° C.
IR $\nu_{max}^{KBr}$cm$^{-1}$: 3070, 2890, 1555, 1510, 1430, 1280.
NMR(d$_6$–DMSO)δ: 7.7(2H, s), 3.8(8H, s).

EXAMPLE 30

1.0 g of 4-(1,3-dithiol-2-ylidene)morpholinium perchlorate was treated in the same manner as in Example 27, and the product was recrystallized from acetone-ethyl ether, whereby 830 mg (yield: 83.0%) of 4-(1,3-dithiol-2-ylidene)morpholinium hydrogen sulfate (Compound No. 30) was obtained as crystals having a melting point of from 120° to 125° C.
IR $\nu_{max}^{KBr}$cm$^{-1}$: 3500, 3100, 1580, 1530, 1440, 1270.
NMR(CD$_3$OD)δ: 7.7(2H, s), 3.8(8H, s).

EXAMPLE 31

1.2 ml of N-methylpiperazine and 1.0 g of 2-methylthio-1,3-dithiolium perchlorate were treated in the same manner as in Example 26, and the product was recrystallized from acetone-ethyl ether, whereby 0.9 g (yield: 74.8%) of 1-(1,3-dithiol-2-ylidene)-4-methylpiperazinium perchlorate (Compound No. 31) was obtained as crystals having a melting point of 192° C.
IR $\nu_{max}^{KBr}$cm$^{-1}$: 3100, 2800, 1560, 1520, 1440, 1300.
NMR(d$_6$–DMSO)δ: 7.6(2H, s), 3.8(4H, t), 2.6(4H, t).

EXAMPLE 32

2.0 g of N-phenylpiperazine and 2.5 g of 2-methylthio-1,3-dithiolium perchlorate were treated in the same manner as in Example 26, and the product was recrystallized from acetone-ethyl ether, whereby 2.7 g (yield: 74.3%) of 1-(1,3-dithiol-2-ylidene)-4-phenylpiperazinium perchlorate (Compound No. 32) was obtained as crystals having a melting point of from 197° to 199° C.

IR $\nu_{max}^{KBr}$cm$^{-1}$: 3070, 1610, 1570, 1510, 1375, 1120, 780, 705.

NMR(d$_6$—DMSO)δ: 7.6(2H, s), 7.4–6.7(5H, m), 4.1–3.8(4H, m), 3.7–3.4(4H, m).

EXAMPLE 33

2.2 g of N-benzylpiperazine and 2.5 g of 2-methylthio-1,3-dithiolium perchlorate were treated in the same manner as in Example 26, and the product was recrystallized from water-ethanol, whereby 2.6 g (yield: 68.9%) of 1-(1,3-dithiol-2-ylidene)-4-benzyl-piperazinium perchlorate (Compound No. 33) was obtained as crystals having a melting point of from 224° to 226° C.

IR $\nu_{max}^{KBr}$cm$^{-1}$: 3070, 1260, 1120, 1110, 1095, 1065.
NMR(d$_6$—DMSO)δ: 7.6(2H, s), 7.3(5H, s), 3.9(4H, t), 3.6(2H, s), 2.7(4H, t).

EXAMPLE 34

1.0 ml of piperidine and 2.5 g of 2-methylthio-1,3-dithiolium perchlorate were treated in the same manner as in Example 26, and the product was recrystallized from acetone-ethyl ether, whereby 2.1 g (yield: 73.6%) of 1-(1,3-dithiol-2-ylidene)piperidinium perchlorate (Compound No. 34) was obtained as crystals having a melting point of from 171° to 172° C.

IR $\nu_{max}^{KBr}$cm$^{-1}$: 3400, 3080, 1620, 1570, 1520, 1440, 1120.
NMR(d$_6$—DMSO)δ: 7.6(2H, s), 3.8(4H, m), 1.7(6H, m).

EXAMPLE 35

0.9 ml of pyrrolidine and 2.5 g of 2-methylthio-1,3-dithiolium perchlorate were treated in the same manner as in Example 26, and the product was recrystallized from acetone-ethyl ether, whereby 1.5 g (yield: 55.3%) of 1-(1,3-dithiol-2-ylidene)pyrrolidinium perchlorate (Compound No. 35) was obtained as crystals having a melting point of 216° C.

IR $\nu_{max}^{KBr}$cm$^{-1}$: 3350, 3100, 1580, 1520, 1450, 1350, 1100.
NMR(d$_6$—DMSO)δ: 7.6(2H, s), 3.7(4H, m), 2.2(4H, m).

EXAMPLE 36

1.0 g of thiazoline and 2.5 g of 2-methylthio-1,3-dithiolium perchlorate were treated in the same manner as in Example 26, and the product was recrystallized from ethanol, whereby 2.3 g (yield: 79.3%) of 3-(1,3-dithiol-2-ylidene)thiazolidinium perchlorate (Compound No. 36) was obtained as crystals having a melting point of from 179° to 180° C.

IR $\nu_{max}^{KBr}$cm$^{-1}$: 3050, 1550, 1105, 1070.
NMR(CD$_3$OD)δ: 7.6(2H, s), 4.8(2H, s), 4.1(2H, t), 3.4(2H, t).

EXAMPLE 37

0.25 g of hexahydroazepine and 0.5 g of 2-methylthio-1,3-dithiolium perchlorate were teated in the same manner as in Example 26, and the product was recrystallized from acetone-ethyl ether, whereby 0.31 g (yield: 52.0%) of 1-(1,3-dithiol-2-ylidene)hexahydroazepinium perchlorate (Compound No. 37) was obtained as crystals having a melting point of from 86° to 88° C.

IR $\nu_{max}^{KBr}$cm$^{-1}$: 3400, 3050, 2930, 1550, 1520, 1480, 1455, 1090.

NMR((CD$_3$)$_2$CO)δ: 7.8(2H, s), 4.0(4H, t), 1.5–2.2(8H, m).

EXAMPLES 38 to 40

The following compounds were prepared in the same manner as in Example 26.

EXAMPLE 38

1-(1,3-dithiol-2-ylidene)-4-ethoxycarbonylpiperazinium perchlorate (Compound No. 38)
mp: 201°–203° C. (recrystallized from methanol).
IR $\nu_{max}^{KBr}$cm$^{-1}$: 3100, 1690, 1570, 1530, 1440.
NMR(d$_6$—DMSO)δ: 1.2(3H, t J=7 Hz), 3.4–4.1(8H, m), 4.1(2H, q J=7 Hz), 7.6(2H, s).

EXAMPLE 39

4-(1,3-dithiol-2-ylidene)thiomorpholinium perchlorate (Compound No. 39)
mp: 214°–215° C. (recrystallized from acetone-ethyl ether).
IR $\nu_{max}^{KBr}$cm$^{-1}$: 3100, 1570, 1522, 1255, 1080, 830.
NMR(d$_6$—DMSO)δ: 2.8–3.05(2H, m), 3.9–4.2(2H, m), 7.7(2H, s).

EXAMPLE 40

1-(1,3-dithiol-2-ylidene)-4-(2-hydroxyethyl)-piperazinium perchlorate (Compound No. 40)
mp: 169°–172° C. (recrystallized from methanol-ethyl ether).
IR $\nu_{max}^{KBr}$cm$^{-1}$: 3120, 2850, 1575, 1530, 1450, 1100.
NMR(d$_6$—DMSO)δ: 2.5–2.85(6H, m), 3.3–4.0(6H, m), 4.4(1H, s), 7.6(2H, s).

EXAMPLE 41

To 30 ml of tetrahydrofuran, 1.4 g of proline ethyl ester was dissolved, and 2.0 g of 2-methylthio-1,3-dithiolium perchlorate was gradually added under stirring at room temperature. The mixture was stirred at room temperature for 1 hour, and the precipitated crystals were collected by filtration and recrystallized from methanol-ethyl ether, whereby 2.1 g (yield: 76%) of 1-(1,3-dithiol-2-ylidene)-2-ethoxycarbonylpyr-rolidinium perchlorate (Compound No. 41) was obtained as crystals having a melting point of from 113° to 114° C.

IR $\nu_{max}^{KBr}$cm$^{-1}$: 3100, 2950, 1743, 1560, 1520, 1230, 1110, 1092.
NMR((CD$_3$)$_2$COCD$_3$)δ: 1.29(3H, t J=7 Hz), 2.10–2.71 (4H, m), 4.01(2H, t J=7 Hz), 4.35(2H, q J=7 Hz), 4.90(1H, d.d J=8 Hz, 3 Hz).

EXAMPLE 42

A solution obtained by dissolving 2.0 g of 1-(1,3-dithiol-2-ylidene)-2-ethoxycarbonylpyrrolidinium perchlorate in 100 ml of water, was passed through a column of 200 cc of an anion exchange resin (Dowex 1-X8 hydrochloride-form), and the fraction containing the desired product was concentrated under reduced pressure. The residue was recrystallized from methanol-ethyl ether, whereby 1.4 g (yield: 86%) of 1-(1,3-dithiol-2-ylidene)-2-ethoxycarbonylpyrrolidinium chloride (Compound No. 42) was obtained as crystals having a melting point of from 135° to 136° C.

IR $\nu_{max}^{KBr}$cm$^{-1}$: 2950, 1743, 1550, 1502, 1229.
NMR(D$_2$O)δ: 1.35(3H, t J=7 Hz), 2.10–2.80(4H, m), 3.95(2H, t J=7 Hz), 4.30(2H, q J=7 Hz), 4.86(1H, m), 7.61(2H, s).

EXAMPLES 43 to 56

The following compounds were prepared in the same manner as in Example 41.

EXAMPLE 43

1-(1,3-dithiol-2-ylidene)-2-(n-hexyl)pyrrolidinium perchlorate (Compound No. 45)

mp: 118°–119° C. (recrystallized from methanol-ethyl ether).

IR $\nu_{max}^{KBr}$cm$^{-1}$: 3080–2950, 1565, 1519, 1118, 1080.

NMR(d$_6$–DMSO)δ: 0.85(3H, t J=7 Hz), 1.05–1.79(10H, m), 2.0–2.37(4H, m), 3.50–4.18(3H, m), 7.64(2H, s).

EXAMPLE 44

1-(1,3-dithiol-2-ylidene)-2-phenylpyrrolidinium perchlorate (Compound No. 46)

mp: 172°–173° C. (recrystallized from methanol-ethyl ether).

IR $\nu_{max}^{KBr}$cm$^{-1}$: 3070, 1550, 1508, 1450, 1080, 765.

NMR(d$_6$–DMSO)δ: 1.88–2.85(4H, m), 3.70–4.49(2H, m), 5.03–5.37(1H, m), 7.40(5H, s), 7.52(1H, d J=7 Hz), 7.68(1H, d J=7 Hz).

EXAMPLE 45

1-(1,3-dithiol-2-ylidene)-3-hydroxymethylpyrrolidinium perchlorate (Compound No. 47)

mp: 68°–70° C. (recrystallized from acetone-ethyl ether).

IR $\nu_{max}^{KBr}$cm$^{-1}$: 3300, 3070, 1570, 1510, 1110, 1075, 725.

NMR(d$_6$–DMSO)δ: 1.87–2.69(3H, m), 3.30–3.94(7H, m), 7.61(2H, s).

EXAMPLE 46

1-(1,3-dithiol-2-ylidene)-2,5-dimethylpyrrolidinium perchlorate (Compound No. 49)

mp: 95°–97° C. (recrystallized from acetone-ethyl ether).

IR $\nu_{max}^{KBr}$cm$^{-1}$: 3075–2970, 1555, 1510, 1120, 1080, 740.

NMR(d$_6$–DMSO)δ: 1.40(6H, d J=7 Hz), 1.85–2.34(4H, m), 3.94–4.19(2H, m), 7.67(2H, s).

EXAMPLE 47

1-(1,3-dithiol-2-ylidene)-3-methylpiperidinium perchlorate (Compound No. 52)

mp: 148°–149° C. (recrystallized from acetone-ethyl ether).

IR $\nu_{max}^{KBr}$cm$^{-1}$: 3080–2925, 1560, 1510, 1420, 1380, 1265, 1120, 1080, 820, 700.

NMR(CD$_3$OD)δ: 1.05(3H, d J=6 Hz), 1.95(5H, m), 3.85(4H, m), 7.53(2H, s).

EXAMPLE 48

1-(1,3-dithiol-2-ylidene)-4-methylpiperidinium perchlorate (Compound No. 53)

mp: 166°–168° C. (recrystallized from acetone-ethyl ether).

IR $\nu_{max}^{KBr}$cm$^{-1}$: 3100–2890, 1570, 1525, 1275, 1090, 835, 720.

NMR(CD$_3$OD)δ: 1.04(3H, d J=6 Hz), 2.03(5H, m), 4.01(4H, m), 7.62(2H, s).

EXAMPLE 49

1-(1,3-dithiol-2-ylidene)-4-ethoxycarbonylpiperidinium perchlorate (Compound No. 56)

mp: 134° C. (recrystallized from acetone-ethyl ether).

IR $\nu_{max}^{KBr}$cm$^{-1}$: 3100–2980, 1735, 1563, 1525, 1460, 1235, 1195, 1110, 1090.

NMR(d$_6$–DMSO)δ: 1.22(3H, t J=7.5 Hz), 2.20(4H, m), 2.75(1H, m), 4.05(4H, m), 4.12(2H, q J=7.5 Hz), 7.67(2H, s).

EXAMPLE 50

1-(1,3-dithiol-2-ylidene)-4-cyanopiperidinium perchlorate (Compound No. 59)

mp: 165°–167° C. (recrystallized from acetone-ethyl ether).

IR $\nu_{max}^{KBr}$cm$^{-1}$: 3100, 2260, 1570, 1100, 820.

NMR(d$_6$–DMSO)δ: 1.70–2.60(4H, m), 3.00–3.50(1H, m), 3.85(4H, t J=7 Hz), 7.60(2H, s).

EXAMPLE 51

1-(1,3-dithiol-2-ylidene)-4-hydroxypiperidinium perchlorate (Compound No. 60)

mp: 171°–173° C. (recrystallized from methanol-ethyl ether).

IR $\nu_{max}^{KBr}$cm$^{-1}$: 3370, 3050, 1565, 1520, 1250, 1090.

NMR(d$_6$–DMSO)δ: 1.52–2.20(4H, m), 3.61–4.05(5H, m), 5.00(1H, s), 7.62(2H, s).

EXAMPLE 52

1-(1,3-dithiol-2-ylidene)-4-acetamidopiperidinium perchlorate (Compound No. 63)

mp: 199°–201° C. (recrystallized from acetone-ethyl ether).

IR $\nu_{max}^{KBr}$cm$^{-1}$: 3240–2950, 1660, 1550, 1150, 1120, 1090, 730.

NMR(d$_6$–DMSO)δ: 1.81(3H, s), 1.51–2.20(4H, m), 3.60–4.20(4H, m), 4.40(1H, br. s), 7.68(2H, s), 7.80(1H, br. s).

EXAMPLE 53

1-(1,3-dithiol-2-ylidene)-3-phenylpiperidinium perchlorate (Compound No. 65)

mp: 153° C. (recrystallized from acetone-ethyl ether).

IR $\nu_{max}^{KBr}$cm$^{-1}$: 3250–2920, 1590, 1460, 1260, 1150, 820, 790, 720.

NMR(d$_6$–DMSO)δ: 3.20–4.20(9H, m), 7.31(5H, s), 7.60(2H, s).

EXAMPLE 54

1-(1,3-dithiol-2-ylidene)-4-benzylpiperidinium perchlorate (Compound No. 66)

mp: 203°–204° C. (recrystallized from acetone-ethyl ether).

IR $\nu_{max}^{KBr}$cm$^{-1}$: 3100–2925, 1565, 1455, 1100, 830, 760.

NMR(d$_6$–DMSO)δ: 1.00–2.10(5H, m), 3.40(2H, s), 3.30–4.20(4H, m), 7.00–7.40(5H, m), 7.60(2H, s).

EXAMPLE 55

1-(1,3-dithiol-2-ylidene)indolinium perchlorate (Compound No. 69)

mp: 210° C. (decomposed) (recrystallized from tetrahydrofuran).

IR $\nu_{max}^{KBr}$cm$^{-1}$: 3080, 1540, 1500, 1470, 1460, 1100, 760, 700.

NMR(d$_6$–DMSO)δ: 3.49(2H, t J=8 Hz), 4.49(2H, t J=8 Hz), 7.30–7.80(4H, m), 7.90(2H, s).

EXAMPLE 56

1-(1,3-dithiol-2-ylidene)benzomorpholinium perchlorate (Compound No. 70)

mp: 210°–212° C. (recrystallized from acetone-ethyl ether).

IR $\nu_{max}^{KBr}$cm$^{-1}$: 3100–2890, 1560, 1500, 1440, 1050, 760.

NMR(d$_6$–DMSO)δ: 3.70–3.90(4H, m), 7.41–7.95(4H, m), 7.85(2H, s).

EXAMPLE 57

To 80 ml of tetrahydrofuran, 1.0 g of proline was suspended, and 2.0 g of 2-methylthio-1,3-dithiolium perchlorate was gradually added thereto under stirring at room temperature. The mixture was stirred at room temperature for 1 hour, and the solvent was distilled off under reduced pressure. The residue was dissolved in a mixture comprising 50 ml of water and 50 ml of ethyl acetate. The aqueous layer was separated and the solvent was distilled off under reduced pressure, whereby 1.6 g (yield: 63%) of 1-(1,3-dithiol-2-ylidene)-2-carboxypyrrolidinium perchlorate (Compound No. 43) was obtained as yellow oily residue.

IR $\nu_{max}^{neat}$cm$^{-1}$: 3100, 1630, 1560, 1520, 1460, 1200, 805.

NMR(d$_6$–DMSO)δ: 2.01–2.41(4H, m), 3.81(2H, t J=6 Hz), 4.67(1H, t J=5 Hz), 7.71(2H, s), 7.52(1H, br. s).

EXAMPLES 58 and 59

The following compounds were prepared in the same manner as in Example 57.

EXAMPLE 58

1-(1,3-dithiol-2-ylidene)-2-ethoxycarbonyl-4-hydroxypyrrolidinium perchlorate (Compound No. 48)
Oily substance.

IR $\nu_{max}^{neat}$cm$^{-1}$: 3500–2980, 1740, 1555, 1505, 1210, 1080.

NMR(d$_6$–DMSO)δ: 1.24(3H, t J=7 Hz), 2.06–2.35(2H, m), 3.10–3.29(1H, m), 4.25(2H, q J=7 Hz), 4.45–4.79(2H, m), 5.07(1H, t J=6 Hz), 7.81(2H, s).

EXAMPLE 59

3-(1,3-dithiol-2-ylidene)-4-ethoxycarbonyl-thiazolidinium perchlorate (Compound No. 50)
Oily substance.

IR $\nu_{max}^{neat}$cm$^{-1}$: 3100–2950, 1742, 1560, 1530, 1240.

NMR(CD$_3$OD)δ: 1.30(3H, t J=7 Hz), 2.61(2H, d J=6 Hz), 4.10(1H, s), 4.31(2H, q J=7 Hz), 4.91(1H, t J=6 Hz), 7.61(2H, s).

EXAMPLE 60

To 30 ml of tetrahydrofuran, 1.6 g of proline amide was dissolved, and 2.0 g of 2-methylthio-1,3-dithiolium iodide was gradually added under stirring at room temperature. The mixture was stirred at room temperature for 1 hour, and the precipitated crystals were collected by filtration and recrystallized from acetone-ethyl ether, whereby 1.3 g (yield: 53%) of 1-(1,3-dithiol-2-ylidene)-2-carbamoylpyrrolidinium iodide (Compound No. 44) was obtained as crystals having a melting point of from 250° to 251° C.

IR $\nu_{max}^{KBr}$cm$^{-1}$: 3400, 3250, 1680, 1485, 1450, 1400, 820.

NMR(d$_6$–DMSO)δ: 2.00–2.40(4H, m), 3.82(2H, t J=7 Hz), 4.50–4.80(1H, m), 7.60(1H, br. s), 7.74(2H, s), 8.12(1H, br. s).

EXAMPLES 61 to 63

The following compounds were prepared in the same manner as in Example 57.

EXAMPLE 61

1-(1,3-dithiol-2-ylidene)-3-ethoxycarbonylpiperidinium iodide (Compound No. 55)
mp: 167° C. (recrystallized from acetone-ethyl ether).

IR $\nu_{max}^{KBr}$cm$^{-1}$: 3075–2850, 1730, 1560, 1520, 1450, 1315 1220, 1030, 825, 700.

NMR(d$_6$–DMSO)δ: 1.18(3H, t J=7.5 Hz), 1.89(4H, m), 3.10(1H, m), 3.95(4H, m), 4.10(2H, q J=7.5 Hz), 7.64(2H, s).

EXAMPLE 62

1-(1,3-dithiol-2-ylidene)-4-carbamoylpiperidinium iodide (Compound No. 58)
mp: 253°–255° C. (recrystallized from acetone-ethyl ether).

IR $\nu_{max}^{KBr}$cm$^{-1}$: 3400, 3250, 1680, 1485, 1450, 1400, 822, 705.

NMR(d$_6$–DMSO)δ: 1.65–2.25(5H, m), 3.70–4.20(4H, m), 6.88(1H, br. s), 7.35(1H, br. s), 7.70(2H, s).

EXAMPLE 63

1-(1,3-dithiol-2-ylidene)-3,5-dimethylpiperidinium iodide (Compound No. 67)
mp: 164°–166° C. (recrystallized from methanol-ethyl ether).

IR $\nu_{max}^{KBr}$cm$^{-1}$: 3510, 3450, 1565, 1520, 1470, 1270, 1075, 820.

NMR(d$_6$–DMSO)δ: 1.00(6H, d J=6 Hz), 1.30–2.30(4H, m), 3.10–4.05(4H, m), 7.63(2H, s).

EXAMPLE 64

To 50 ml of tetrahydrofuran, 1.1 g of α-pipecoline was dissolved, and 2.0 g of 2-methylthio-1,3-dithiolium perchlorate was gradually added thereto under stirring at room temperature. The mixture was stirred at room temperature for 1 hour, and then 50 ml of ethyl ether was added thereto, whereby 1.5 g (yield: 80%) of 1-(1,3-dithiol-2-ylidene)-2-methylpiperidinium perchlorate (Compound No. 51) was obtained as yellow oily precipitates.

IR $\nu_{max}^{neat}$cm$^{-1}$: 3100–2980, 1560, 1520, 1450, 1100, 650.

NMR(d$_6$–DMSO)δ: 1.00–2.10(9H, m), 2.70–4.00(3H, m), 7.55(2H, s).

EXAMPLES 65 and 66

The following compounds were prepared in the same manner as in Example 64.

EXAMPLE 65

1-(1,3-dithiol-2-ylidene)-2-ethoxycarbonylpiperidinium perchlorate (Compound No. 54)
Oily substance.

IR $\nu_{max}^{neat}$cm$^{-1}$: 3100, 1735, 1440, 1280, 1100.

NMR(d$_6$–DMSO)δ: 1.20(3H, t J=7 Hz), 1.20–2.40(6H, m), 2.80–3.80(3H, m), 4.26(2H, q J=7 Hz), 7.70(2H, s).

EXAMPLE 66

1-(1,3-dithiol-2-ylidene)-3-ethoxycarbonyl-6-methyl-piperidinium perchlorate (Compound No. 68)
Oily substance.

IR $\nu_{max}{}^{neat}$cm$^{-1}$: 3100-3000, 1720, 1557, 1510, 1380, 1210, 1080.

NMR(d$_6$-DMSO)δ: 1.00-1.50(6H, m), 1.50-2.10(4H, m), 2.60-3.00(1H, m), 3.00-3.60(1H, m), 3.60-4.50(4H, m), 7.68(2H, s).

EXAMPLE 67

To 5 ml of dimethylformamide, 2.0 g of 2-methylthio-1,3-dithiolium perchlorate was suspended, and 1.2 g of isonipecotic acid was gradually added thereto under stirring at room temperature. The mixture was stirred at room temperature for 1 hour, and after an addition of 60 ml of ethyl acetate, the precipitated crystals were collected by filtration and recrystallized from acetone-ethyl ether, whereby 1.6 g (yield: 61%) of 1-(1,3-dithiol-2-ylidene)-4-carboxypiperidinium perchlorate (Compound No. 57) was obtained as crystals having a melting point of from 170° to 172° C.

IR $\nu_{max}{}^{KBr}$cm$^{-1}$: 3100-2940, 1720, 1580, 1420, 1245.

NMR(d$_6$-DMSO)δ: 1.95-2.15(4H, m), 2.66-2.74(1H, m), 3.85(4H, t J=6 Hz), 7.59(2H, s), 7.6(1H, br. s).

EXAMPLE 68

To 40 ml of tetrahydrofuran, 1.4 g of 1,2-dimethylpiperazine was dissolved, and 2.0 g of 2-methylthio-1,3-dithiol perchlorate was gradually added thereto under stirring at room temperature. The mixture was stirred at room temperature for 1 hour, and after an addition of 30 ml of ethyl ether, the precipitated crystal powder was collected by filtration, whereby 1.6 g (yield: 60%) of 4-(1,3-dithiol-2-ylidene)-1,2-dimethylpiperazinium perchlorate (Compound No. 71) was obtained as crystals having a melting point of from 48° to 50° C.

IR $\nu_{max}{}^{KBr}$cm$^{-1}$: 2900, 1460, 1420, 1140, 1110, 1090.

NMR(d$_6$-DMSO)δ: 1.07(3H, d J=7 Hz), 2.28(3H, s), 2.40-2.80(2H, m) 3.50-4.20(5H, m), 7.70(2H, s).

EXAMPLE 69

The following compound was prepared in the same manner as in Example 41.

1-(1,3-dithiol-2-ylidene)-4-(N',N'-dimethylamino)-piperidinium perchlorate (Compound No. 64)

mp: 223° C. (recrystallized from methanol).

IR $\nu_{max}{}^{KBr}$cm$^{-1}$: 3100, 1570, 1460, 1270, 1090, 835, 690.

NMR(d$_6$-DMSO)δ: 1.80-2.31(4H, m), 2.74(6H, s) 3.10-4.32(5H, m), 7.64(2H, s).

The compounds of the present invention exhibit the curing and preventive effects against liver diseases accompanying centrilobular necrosis of the liver, the curing and preventive effects against liver diseases accompanying peripheral lobular death, the curing effects against hepatitis accompanying mesenchyme reaction with sporadic hepatic necrosis, the curing effects against congestion of the liver and the effects for the promotion of secretory of bile and bile acids.

Thus, the compounds of the formula I of the present invention are effective as a drug for restoring or stimulating the liver functions for a liver suffered from the reduction of the parenchyma cell number and function and from the accompanying lobular necrosis. Thus, they are useful for the treatment or prevention of liver deseases.

We claim:

1. A 1,3-dithiole derivative having the formula:

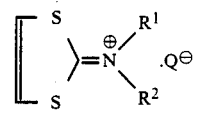

wherein R$^1$ and R$^2$ together form an alkylene or alkenylene group having from 3 to 6 carbon atoms, or a hetero atom selected from the group consisting of an oxygen atom, a sulfur atom and a nitrogen atom which may have a substituent selected from the group consisting of a lower alkyl group, a lower alkenyl group, a lower alkynyl group, a lower alkoxycarbonyl group, a hydroxy-substituted lower alkyl group, an aryl group and an aralkyl group, and said alkylene or alkenylene group being substituted by one or two substituents selected from the group consisting of a lower alkyl group, a carboxyl group, a lower alkoxycarbonyl group, and a

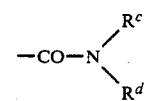

group wherein each of R$^c$ and R$^d$ is a hydrogen atom, a lower alkyl group, an aryl group or an aralkyl group, provided that at least one substituent on the alkylene or alkenylene group is a carboxyl, loweralkoxycarbonyl or

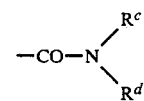

group, and Q is an acid residue.

2. The 1,3-dithiole derivative according to claim 1, wherein R$^1$ and R$^2$ together form —(CH$_2$)$_4$—, —(CH$_2$)$_5$—, —(CH$_2$)$_6$—, —CH$_2$OCH$_2$CH$_2$—, —CH$_2$SCH$_2$CH$_2$—, —CH$_2$CH$_2$SCH$_2$CH$_2$—, —CH$_2$CH$_2$OCH$_2$CH$_2$—, —CH$_2$CH$_2$NHCH$_2$CH$_2$—, —CH$_2$CH$_2$N(Ph)CH$_2$CH$_2$—, —CH$_2$CH$_2$N(CH$_2$Ph)CH$_2$CH$_2$—, —CH$_2$CH$_2$N(CH$_3$)CH$_2$CH$_2$—, —CH$_2$CH=CHCH$_2$—, —CH$_2$CH=CHCH$_2$CH$_2$—, which may be substituted by carboxyl, methyl, ethyl, n-propyl, isopropyl, n-butyl, n-pentyl, n-hexyl, methoxycarbonyl, ethoxycarbonyl, isopropoxycarbonyl, carbamoyl, N-methylcarbamoyl, N,N-dimethylcarbamoyl, N-phenylcarbamoyl or N-benzylcarbamoyl, and Q is an acid residue of hydrochloric acid, hydrobromic acid, hydroiodic acid, nitric acid, perchloric acid, borofluoric acid, sulfuric acid, phosphoric acid, oxalic acid, tartaric acid, citric acid, methanesulfonic acid or p-toluenesulfonic acid.

3. The 1,3-dithiole derivative according to claim 1, wherein the

moiety is 2-ethoxycarbonylpyrrolidinium, 2-carboxypyrrolidinium, 2-carbamoylpyrrolidinium, 4-ethoxycarbonylthiazolidinium, 2-ethoxycarbonylpiperidinium, 3-ethoxycarbonylpiperidinium, 4-ethoxycarbonylpiperidinium, 4-carboxypiperidinium, 4-carbamoylpiperidinium, 3-ethoxycarbonyl-6-methylpiperidinium or 4-ethoxycarbonylpiperazinium, and Q is ClO$_4$, Cl, Br, I or HSO$_4$.

4. A pharmaceutical composition for treating liver diseases, which comprises an effective amount of a 1,3-dithiole derivative of the formula I as defined in claim 1 and a pharmaceutically acceptable carrier or diluent.

* * * * *